United States Patent
Gerold

(10) Patent No.: US 9,427,500 B2
(45) Date of Patent: *Aug. 30, 2016

(54) STENT MADE OF A COBALT ALLOY

(71) Applicant: BIOTRONIK AG, Buelach (CH)

(72) Inventor: Bodo Gerold, Karlstadt (DE)

(73) Assignee: BIOTRONIK AG, Beulach (CH)

(*) Notice: Subject to any disclaimer, the term of this patent is extended or adjusted under 35 U.S.C. 154(b) by 519 days.

This patent is subject to a terminal disclaimer.

(21) Appl. No.: 13/913,816

(22) Filed: Jun. 10, 2013

(65) Prior Publication Data

US 2013/0336836 A1    Dec. 19, 2013

Related U.S. Application Data

(60) Provisional application No. 61/660,820, filed on Jun. 18, 2012.

(51) Int. Cl.
  *A61L 31/02*   (2006.01)
  *C22C 19/07*   (2006.01)
  *C22F 1/10*    (2006.01)

(52) U.S. Cl.
  CPC ............... *A61L 31/022* (2013.01); *C22C 19/07* (2013.01); *C22F 1/10* (2013.01)

(58) Field of Classification Search
  CPC ......... A61L 31/022; C22C 19/07; C22F 1/10
  USPC ....................................................... 420/440
  See application file for complete search history.

(56) References Cited

U.S. PATENT DOCUMENTS 4,116,724 A * 9/1978 Hirschfeld ............... C22C 19/07
                                                       148/425
6,756,012 B2 * 6/2004 Prasad ..................... A61K 6/046
                                                       148/425
2013/0338757 A1 * 12/2013 Gerold ...................... A61F 2/06
                                                       623/1.15

FOREIGN PATENT DOCUMENTS

WO    WO 0172349 A1 * 10/2001   ........... A61L 31/022

* cited by examiner

Primary Examiner — Jie Yang
(74) Attorney, Agent, or Firm — Wagenknecht IP Law Group PC

(57) ABSTRACT

A stent made entirely or partially of a cobalt alloy having the following composition:

Co: 18.36-66.85% by weight
Cr: 17.0-30.0% by weight
Mn: 4.0-10.0% by weight
W: 9.0-18.0% by weight
Fe: 3.0-20.0% by weight
C: 0.03-0.5% by weight
N: 0.1-1.0% by weight
Si: 0-2.0% by weight
O: 0-0.05% by weight with the alloying components and production-related impurities adding up to 100% by weight and (i) a PRE value for corrosion resistance, which is derived from the weight percentages of the alloying components according to formula (1)

$$PRE=[Cr]+1.65\times[W]+30\times[N] \quad (1)$$

ranges between 34 and 89; and (ii) for the contents of nitrogen and carbon the following restrictions according to formula (2) and (3) apply $$0.15 \leq C+N \leq 1.00 \quad (2)$$

$$0.25 \leq C+N \leq 1.00 \quad (3).$$

15 Claims, No Drawings

STENT MADE OF A COBALT ALLOY

CROSS REFERENCE TO RELATED APPLICATIONS

This invention claims benefit of priority to U.S. provisional patent application Ser. No. 61/660,820 filed Jun. 18, 2012; the entire content of which is herein incorporated by reference in its entirety.

TECHNICAL FIELD

The invention relates to a stent which is made entirely or partially of a cobalt alloy.

BACKGROUND

The implantation of stents has become established as one of the most effective therapeutic measures for the treatment of vascular diseases. Stents have the purpose of performing a stabilizing function in hollow organs of a patient. For this purpose, stents featuring conventional designs have a filigree supporting structure comprising metal braces, which is initially present in compressed form for introduction into the body and is expanded at the site of the application. One of the main application areas of such stents is to permanently or temporarily dilate and hold open vascular constrictions, particularly constrictions (stenoses) of the coronary blood vessels. In addition, aneurysm stents are also known, which are used primarily to seal the aneurysm.

Stents have a peripheral wall with sufficient load-bearing capacity in order to hold the constricted vessel open to the desired extent and a tubular base body through the blood continues to flow without impairment. The peripheral wall is generally formed by a lattice-like supporting structure, which allows the stent to be introduced in a compressed state, in which it has a small outside diameter, all the way to the stenosis of the particular vessel to be treated and to be expanded there, for example by way of a balloon catheter, so that the vessel has the desired, enlarged inside diameter. As an alternative, shape memory materials such as nitinol have the ability to self-expand when a restoring force is eliminated that keeps the implant at a small diameter. The restoring force is generally applied to the material by a protective tube.

The stent has a base body made of an implant material. An implant material is a non-living material, which is used for applications in medicine and interacts with biological systems. A basic prerequisite for the use of a material as implant material, which is in contact with the body area when used as intended, is the body friendliness thereof (biocompatibility). Biocompatibility shall be understood as the ability of a material to evoke an appropriate tissue response in a specific application. This includes an adaptation of the chemical, physical, biological, and morphological surface properties of an implant to the recipient's tissue with the aim of a clinically desirable interaction. The biocompatibility of the implant material is also dependent on the temporal course of the response of the biosystem in which it is implanted. For example, irritations and inflammations occur in a relatively short time, which can lead to tissue changes. As a function of the properties of the implant material, biological systems thus react in different ways. According to the response of the biosystem, the implant materials can be divided into bioactive, bioinert and degradable/resorbable (referred to here as biocorrodible) materials.

Implant materials comprise polymers, metallic materials, and ceramic materials (as coatings, for example). Biocompatible metals and metal alloys for permanent implants comprise, for example, stainless steels (such as 316L), cobalt-based alloys (such as CoCrMo cast alloys, CoCrMo forge alloys, CoCrWNi forge alloys and CoCrNiMo forge alloys), technical pure titanium and titanium alloys (such as cp titanium, TiAl6V4 or TiAl6Nb7) and gold alloys. In the field of biocorrodible stents, the use of magnesium or technical pure iron as well as biocorrodible base alloys of the elements magnesium, iron, zinc, molybdenum, and tungsten are proposed. The present invention relates to non-biodegradable implant materials, in particular cobalt-based alloys.

Stents must have the ability to tolerate large plastic elongation and maintain the size or diameter thereof when they are expanded. In general, the ideal stent should:
- have a low profile; this includes the suitability of being crimped onto a balloon catheter;
- exhibit good expansion properties; when the stent is introduced in the lesion and the balloon is inflated, the stent should uniformly expand so as to adapt to the vessel wall;
- have sufficient radial strength and negligible recoil; once the stent has been placed, it should withstand the restoring forces of the atherosclerotic vessel wall and not collapse;
- have sufficient flexibility to bending; the stent can thus also be delivered through vessels and stenoses having smaller diameters;
- have adequate radiopacity or MRI compatibility; the medical staff can thus assess the implantation and position of the stent in vivo;
- have low thrombogenicity; the material should be biocompatible and in particular prevent the deposition and agglutination of platelets;
- have the option of releasing active agents; this is used in particular for preventing restenosis.

The requirements address in particular the mechanical properties of the material of which the stent is produced. The classic 316L, MP53N and L-605 materials that are used for constructing balloon-expandable stents have mechanical disadvantages which restrict the freedom in stent design development and in use:

(i) insufficient (ultimate) tensile strength UTS and elongation at fracture E
  As a result, the collapse pressure and radial strength are lower, so that thicker stent struts are required, which causes a larger loss of lumen during implantation, delays healing (endothelialization) into the vascular wall, and restricts the freedom in the geometric stent design development. Thicker struts additionally make the stent more rigid, which reduces the flexibility around bends.

(ii) yield tensile strength YTS too high
  This result in high elastic rebound, which worsens the crimpability, leads to a thicker crimp profile and causes higher recoil (loss of lumen due to expansion).

Moreover, the biocompatibility of the material must be ensured. Nickel has been repeatedly listed as causing allergies or local and systemic incompatibilities. A need therefore exists for nickel-free materials for medical use.

DE 197 04 530 A1 describes a nickel-free, austenitic cobalt-based alloy for avoiding allergies in various objects of use, including implants, having high corrosion resistance and good formability. Here, nickel is replaced as the stabilizer for the austenitic state by adding titanium and/or niobium (together 4 to 6% by weight). The alloy additionally contains Cr (10 to 18% by weight), Fe (5 to 20% by weight), and Mo and W (together 4 to 8% by weight, with the content of W being half that of Mo). Moreover, the alloy can contain Cu (0 to 2% by weight), Mn (0 to 3% by weight), Al (0 to 3% by weight), Si, (0 to 1% by weight), C (0 to 0.1% by weight) and N (0 to 0.1% by weight). The disadvantages of this alloy are insufficient ductility and, more particularly, insufficient radiopacity for the use as a stent material. In addition, Cu and Al are not considered to be biocompatible.

U.S. Pat. No. 3,865,585 describes a nickel-free cobalt-based alloy comprising Cr (26 to 31% by weight), Mo (4 to 6.5% by weight), Si (0 to 2% by weight), Fe (0 to 1% by weight), B (0 to 0.5%) by weight, C (0 to 0.5% by weight), N (0.15 to 0.5% b weight), with the cumulative content of C and N not exceeding 0.7% by weight. However, at less than 20%, the ductility of the alloy is very low and not suited for stents.

DE 36 24 377 A1 proposes a cobalt-based alloy having the following composition for medical implants and fixed dental prostheses: Cr (15 to 24% by weight), Fe (2 to 15% by weight), Mo (3 to 10% by weight), N (0 to 0.05% by weight) and C (0 to 0.05% by weight). At approximately 10%, the ductility is very low and not suited for stents.

A continued need thus exists for a nickel-free metallic implant material that has sufficiently high ductility and is suited for the production of stents.

DETAILED DESCRIPTION

The stent according to the invention solves or mitigates one or more of the above-described problems. The stent is made entirely or partially of a cobalt alloy having the following composition:

Co: 18.36-66.85% by weight
Cr: 17.0-30.0% by weight
Mn: 4.0-10.0% by weight
W: 9.0-18.0% by weight
Fe: 3.0-20.0% by weight
C: 0.03-0.5% by weight
N: 0.1-1.0% by weight
Si: 0-2.0% by weight
O: 0-0.05% by weight with the alloying components listed above and production-related impurities adding up to 100% by weight and (i) a PRE value for corrosion resistance, which is derived from the weight percentages of the aforementioned alloying components according to formula (1)

$$PRE=[Cr]+1.65\times[W]+30\times[N] \quad (1)$$

ranges between 34 and 89, preferably between 46 and 73, with 46 to 58 being particularly preferred; and (ii) for the contents of nitrogen and carbon the following restrictions according to formulas (2) and (3) apply $$0.15 \leq C+N \leq 1.00 \quad (2)$$

$$0.25 \leq C+N \leq 1.00 \quad (3).$$

The cobalt-based alloys used according to the invention are corrosion-resistant, friction wear-resistant and have high tensile strength, which can be increased even further by suitable heat treating methods, and also have high ductility and excellent radiopacity. The remaining alloying components stabilize the austenite, so that the alloy is preferably present entirely in austenitic modification.

The alloys used according to the invention exhibit very high tensile strength UTS of >1000 MPa, and preferably >1100 MPa. The high tensile strength makes it possible to produce thin structures in the stent design, which nonetheless give the stent high radial strength of >1.5 bar (150 kPa).

The alloys used according to the invention further exhibit a very pronounced strain-hardening behavior, which is expressed in the yield ratio YTS/UTS, which should be particularly small. YTS/UTS should be <0.75, preferably <0.60, with <0.55 being particularly preferred. This property is particularly significant for controlling the deformation during crimping and during the stent expansion. A homogeneous opening behavior is desirable, which depends not only on the mechanical properties of the material, but also the stent design, which in turn can be developed with greater freedom if the mechanical properties of the material allow.

The alloys according to the invention further exhibit excellent formability at room temperature. The degree of deformation (elongation at fracture) At is >40%, preferably >50%, and more particularly >60%.

The alloys according to the invention can additionally be hardened by suitable, in particular multi-stage, heat treating methods.

This produces austenitic CoCrMnWFe alloys which are free of Ni. Stents produced, from this material have higher radial strength, a homogeneous opening behavior, greater dilation reserves (nominal diameter +0.5 mm) and better crimpability (lower diameter), while having a reduced strut cross-section (better endothelialization behavior) than conventional stents. Given the freedom of nickel, the biocompatibility is significantly improved. In addition, the resistance to pitting, abrasion and fretting is improved, in particular in situations in which two or more stents overlap each other.

As nickel replacement, the elements C, N and Mn moreover are used to stabilize the austenitic (face-centered cubic) state.

A content of Mn in the alloy is preferably 6.0 to 10.0% by weight, and more particularly 7.0 to 9.0% by weight.

Moreover, it is preferred if a content of Fe in the alloy is 5.0 to 12.0% by weight, and more particularly 7.5 to 10.5% by weight.

The content of C in the alloy is preferably 0.03 to 0.06% by weight.

It is also preferred if a content of N in the alloy is 0.1 to 0.5% by weight, and more particularly 0.1 to 0.2% by weight.

Moreover, it is preferred if a content of Cr in the alloy is 20.0 to 28.0% by weight, and more particularly 21.0 to 26.0% by weight. Chromium in solid solution increases the tensile strength. However, chromium also plays a key role in the corrosion and oxidation resistance. A high content of chromium means high corrosion resistance. The alloys according to the invention thus have high resistance to local corrosion, referred to as pitting. This resistance is described by the PRE (pitting resistance equivalent) value. The PRE is in the range of 34 to 89, preferably 46 to 73, with 46 to 58 being particularly preferred.

Sulfur reduces the PRE, and thus the resistance to pitting, by a factor of 335 and phosphorus does to by a factor of 1,000. It is therefore preferred for the cumulative contamination with P and S not to exceed 0.03% by weight.

Moreover, it is preferred if a content of W in the alloy is 14.0 to 18.0% by weight, and more particularly 14.5 to 15.5% by weight. In addition to solid solution hardening and the increase in friction resistance due to tungsten, the increased material density of tungsten in particular in the application as a vascular support is advantageous, because good radiopacity is achieved. In addition, tungsten contributes to the corrosion resistance.

A content of Si in the alloys is preferably 0.10 to 0.25% by weight, and more particularly 0.12 to 0.16% by weight.

The invention further relates to the use of the aforementioned cobalt alloy for producing a stent, which includes providing the cobalt alloy and forming a stent therefrom.

The alloys can be produced analogously to the customary production methods for cobalt-based alloys.

Exemplary Embodiment 1
Co-22Cr-15W-8Fe-8Mn-0.15Si-0.15N-0.05C
PRE=51.25
Mechanical properties in the recrystallized state after annealing at approximately 1200° C.:
YTS=500-550 MPa
UTS=1000-1050 MPa
A>60%

Exemplary Embodiment 2
Co-25Cr-10W-10Fe-8Mn-0.2Si-0.2N-0.05C
PRE=46.0
Mechanical properties in the recrystallized state after annealing at approximately 1200° C.:
YTS>550 MPa
UTS>1100 MPa
E=40-45%

Exemplary Embodiment 3
Co-25Cr-15W-10Fe-8Mn-0.2Si-0.15N-0.05C
PRE=54.25
Mechanical properties in the recrystallized state after annealing at approximately 1200° C.:
YTS>550 MPa
UTS>1100 MPa
E=40-45%

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A stent comprising a filigree support structure made entirely or partially of a nickel-free cobalt alloy comprising a tensile strength of greater than 1000 MPa and having the following composition:
   alloying components comprising:
   Co: 18.36-66.85% by weight
   Cr: 17.0-30.0% by weight
   Mn: 7.0-10.0% by weight
   W: 9.0-18.0% by weight
   Fe: 3.0-20.0% by weight
   C: 0.03-0.5% by weight
   N: 0.1-1.0% by weight
   Si: 0-2.0% by weight
   O: 0-0.05% by weight
   with the alloying components and production-related impurities adding up to 100% by weight;
   (i) a PRE value for corrosion resistance, which is derived from the weight percentages of the alloying components according to formula (1)

$$PRE=[Cr]+1.65\times[W]+30\times[N] \quad (1)$$

ranges between 34 and 89; and
   (ii) the contents of nitrogen and carbon are restricted according to formula (2)

$$0.15 \leq C+N \leq 1.00 \quad (2).$$

2. The stent according to claim 1, wherein a content of Cr in the alloy is 20.0 to 28.0% by weight.

3. The stent according to claim 1, wherein a content of Mn in the alloy is 7.0 to 9.0% by weight.

4. The stent according to claim 1, wherein a content of W in the alloy is 14.0 to 18.0% by weight.

5. The stent according to claim 1, wherein a content of Fe in the alloy is 5.0 to 12.0% by weight.

6. The stent according to claim 1, wherein a content of Si in the alloy is 0.10 to 0.25% by weight.

7. The stent according to claim 1, wherein a content of C in the alloy is 0.03 to 0.06% by weight.

8. The stent according to claim 1, wherein a content of N in the alloy is 0.1 to 0.5% by weight.

9. The stent according to claim 1, wherein the PRE value ranges between 46 and 73.

10. The stent according to claim 1, wherein a cumulative contamination with P and S does not exceed 0.03% by weight.

11. A method of forming a stent comprising:
   a) providing a nickel free cobalt alloy comprising a tensile strength of greater than 1000 MPa and having the composition:
   alloying components comprising:
   Co: 18.36-66.85% by weight
   Cr: 17.0-30.0% by weight
   Mn: 4.0-10.0% by weight
   W: 9.0-18.0% by weight
   Fe: 3.0-20.0% by weight
   C: 0.03-0.5% by weight
   N: 0.1-1.0% by weight
   Si: 0-2.0% by weight
   O: 0-0.05% by weight
   with the alloying components and production-related impurities adding up to 100% by weight;
   (i) a PRE value for corrosion resistance, which is derived from the weight percentages of the alloying components according to formula (1)

$$PRE=[Cr]+1.65\times[W]+30\times[N] \quad (1)$$

ranges between 34 and 89;
   (ii) the contents of nitrogen and carbon are restricted according to formula (2)

$$0.15 \leq C+N \leq 1.00 \quad (2);$$

and
   b) forming a filigree support structure as a stent from the cobalt alloy.

12. A stent comprising a filigree support structure made entirely or partially of a cobalt alloy comprising a tensile strength of greater than 1000 MPa and having the following composition:
   alloying components comprising:
   Co: 18.36-66.85% by weight
   Cr: 17.0-30.0% by weight
   Mn: 4.0-10.0% by weight
   W: 9.0-18.0% by weight
   Fe: 7.5-10.5% by weight
   C: 0.03-0.5% by weight
   N: 0.1-1.0% by weight
   Si: 0-2.0% by weight
   O: 0-0.05% by weight
   with the alloying components and production-related impurities adding up to 100% by weight;
   (i) a PRE value for corrosion resistance, which is derived from the weight percentages of the alloying components according to formula (1)

$$PRE=[Cr]+1.65\times[W]+30\times[N] \quad (1)$$

ranges between 34 and 89; and (ii) the contents of nitrogen and carbon are restricted according to $$0.15 \leq C+N \leq 1.00 \qquad (2).$$

13. The stent according to claim 12, wherein the cobalt alloy is a nickel-free cobalt alloy.

14. The stent according to claim 13, wherein a content of Mn in the alloy is 7.0 to 10.0% by weight.

15. The stent according to claim 14, wherein the content of Mn in the alloy is 7.0 to 9.0% by weight.

* * * * *